(12) United States Patent
Emmott et al.

(10) Patent No.: US 8,235,950 B2
(45) Date of Patent: Aug. 7, 2012

(54) SAFETY NEEDLE

(75) Inventors: Douglas Arthur Emmott, Suffolk (GB); Judith Mary Weston, Norfolk (GB); Terence Edward Weston, Swannington (GB)

(73) Assignee: Salvus Technology GmbH, Stradbroke, Suffolk (GB)

( * ) Notice: Subject to any disclaimer, the term of this patent is extended or adjusted under 35 U.S.C. 154(b) by 500 days.

(21) Appl. No.: 11/815,475

(22) PCT Filed: Feb. 3, 2005

(86) PCT No.: PCT/GB2005/000357
§ 371 (c)(1),
(2), (4) Date: Aug. 3, 2007

(87) PCT Pub. No.: WO2006/082350
PCT Pub. Date: Aug. 10, 2006

(65) Prior Publication Data
US 2008/0200881 A1    Aug. 21, 2008

(51) Int. Cl.
*A61M 5/32* (2006.01)
(52) U.S. Cl. ........ 604/192; 604/110; 604/198; 604/199; 604/263
(58) Field of Classification Search .................. 604/110, 604/111, 192–199, 263, 171, 117
See application file for complete search history.

(56) References Cited

U.S. PATENT DOCUMENTS

| | | | |
|---|---|---|---|
| 1,845,036 A | 2/1932 | Busher | |
| 3,114,455 A | 12/1963 | Claisse et al. | |
| 3,134,380 A | 5/1964 | Armao | |
| 3,677,245 A | 7/1972 | Welch | |
| 4,553,541 A | 11/1985 | Burns | |
| 4,735,203 A | 4/1988 | Ryder et al. | |
| 4,795,432 A | 1/1989 | Karczmer | |
| 4,813,940 A | 3/1989 | Parry | |
| 4,850,996 A | 7/1989 | Cree | |
| 4,911,693 A | 3/1990 | Paris | |
| 4,927,019 A | 5/1990 | Smedley et al. | |

(Continued)

FOREIGN PATENT DOCUMENTS
CN        1777453 A    5/2006
(Continued)

OTHER PUBLICATIONS

Third Chinese Office Action for related Chinese Patent Application No. 200480006925.1; dated Jul. 10, 2009; English translation only (3 pages).

(Continued)

*Primary Examiner* — Bhisma Mehta
*Assistant Examiner* — Kami A Bosworth
(74) *Attorney, Agent, or Firm* — Panitch Schwarze Belisario & Nadel LLP (57) ABSTRACT

A safety needle pack to prevent needle stick injuries includes a hollow needle, a needle hub, a slidable sleeve mounted on the needle hub and a pack surrounding the needle, hub and sleeve. The slidable sleeve is adapted to slide between an extended position in which the injection end of the needle is located inside the slidable sleeve and a retracted position in which the injection end of the needle projects from the slidable sleeve. The pack is releasably mounted on the needle hub and slidable sleeve such that the injection end of the pack covers the tip of needle.

26 Claims, 9 Drawing Sheets

U.S. PATENT DOCUMENTS

| | | | |
|---|---|---|---|
| 5,015,240 A | | 5/1991 | Charmasson et al. |
| 5,104,384 A | | 4/1992 | Parry |
| 5,219,339 A | | 6/1993 | Saito |
| 5,242,401 A | | 9/1993 | Colsky |
| 5,312,366 A | | 5/1994 | Vailancourt |
| 5,336,197 A | | 8/1994 | Kuracina et al. |
| 5,385,561 A | | 1/1995 | Cerny |
| 5,421,347 A | | 6/1995 | Enstrom |
| 5,549,568 A | | 8/1996 | Shields |
| 5,601,535 A | * | 2/1997 | Byrne et al. .................. 604/198 |
| 5,658,256 A | | 8/1997 | Shields |
| 5,669,888 A | * | 9/1997 | Trapp ............................ 604/263 |
| 5,755,696 A | | 5/1998 | Caizza et al. |
| 5,891,103 A | * | 4/1999 | Burns ........................... 604/192 |
| 5,910,130 A | | 6/1999 | Caizza et al. |
| 5,944,699 A | | 8/1999 | Barrelle et al. |
| 5,971,966 A | * | 10/1999 | Lav ............................... 604/263 |
| 6,203,529 B1 | | 3/2001 | Gabriel et al. |
| 6,210,374 B1 | * | 4/2001 | Malencheck ................. 604/192 |
| 6,261,264 B1 | * | 7/2001 | Tamaro ......................... 604/198 |
| 6,331,174 B1 | | 12/2001 | Spallek et al. |
| 6,398,762 B1 | | 6/2002 | Otto et al. |
| 6,511,460 B1 | * | 1/2003 | Arnissolle ..................... 604/197 |
| 6,537,259 B1 | | 3/2003 | Niermann |
| 6,685,676 B2 | | 2/2004 | Jansen et al. |
| 7,041,086 B2 | | 5/2006 | Yang |
| 7,182,734 B2 | | 2/2007 | Saulenas et al. |
| 7,223,258 B2 | | 5/2007 | Crawford |
| 7,713,280 B2 | | 5/2010 | Marshall et al. |
| 2002/0004648 A1 | | 1/2002 | Larsen et al. |
| 2002/0087180 A1 | | 7/2002 | Searle et al. |
| 2003/0014018 A1 | | 1/2003 | Giambattista et al. |
| 2003/0144633 A1 | | 7/2003 | Kirchhofer |
| 2004/0116877 A1 | * | 6/2004 | Yang ............................. 604/263 |
| 2004/0210196 A1 | | 10/2004 | Bush, Jr. et al. |
| 2005/0038391 A1 | | 2/2005 | Wittland et al. |
| 2006/0129173 A1 | | 6/2006 | Wilkinson |
| 2006/0167411 A1 | | 7/2006 | Weston et al. |
| 2008/0183140 A1 | | 7/2008 | Paproski et al. |

FOREIGN PATENT DOCUMENTS

| | | |
|---|---|---|
| EP | 0467173 | 1/1992 |
| EP | 0744183 A2 | 11/1996 |
| EP | 0815884 A1 | 1/1998 |
| EP | 1252907 | 10/2002 |
| EP | 1447108 A1 | 8/2004 |
| EP | 1535640 A | 6/2005 |
| EP | 1558311 | 8/2005 |
| FR | 2701848 A1 | 2/1993 |
| JP | 3158171 A | 7/1991 |
| WO | 91/11212 A | 8/1991 |
| WO | 9400172 A1 | 1/1994 |
| WO | 9419036 A1 | 9/1994 |
| WO | 01/76665 A | 10/2001 |
| WO | 01/91837 A | 12/2001 |
| WO | 02/089878 A | 11/2002 |
| WO | 02/100467 A | 12/2002 |
| WO | 03/066141 | 8/2003 |
| WO | 04/000397 A | 12/2003 |
| WO | 2004/071560 A | 8/2004 |
| WO | 2004069302 A2 | 8/2004 |
| WO | WO2004071560 A1 | 8/2004 |
| WO | WO2006090118 A1 | 8/2006 |
| WO | 2008067467 A2 | 6/2008 |

OTHER PUBLICATIONS

International Search Report for the corresponding International Patent Application No. PCT/GB2004/000516; mailed May 27, 2004; 2 pages.
Office Action for the related U.S. Appl. No. 10/545,160 issued Aug. 8, 2009.
Examination Report for the related Australian Patent Application No. 2004212245, dated Nov. 11, 2008.
First Chinese Office Action for the related Chinese Patent Application No. 200480006925.1; dated Dec. 28, 2007; English translation only (5 pages).
The second Chinese Office Action for the related Chinese Patent Application No. 200480006925.1; dated Feb. 20, 2009; English translation only (3 pages).
European Search Report for the related European Patent Application No. 03 25 2192, dated May 26, 2003; 4 pages.
Japanese Office Action for the related Japanese Patent Application No. 2006-502257, issued Sep. 11, 2009.
First Chinese Office Action for the related Chinese Patent Application No. 2005800477077, issued Sep. 25, 2009.
Written Opinion issued May 27, 2004 in International Patent Application PCT/GB2004/000516.
European Search Report issued on Oct. 4, 2010 in European Patent Application No. EP 09 17 5295.
Partial European Search Report for the related European Application No. 09175295.6 dated Apr. 9, 2010.
Chinese Office Action for the related Chinese Application No. 200680006138.6 dated Apr. 15, 2010.
Office Action Issued Apr. 29, 2011 in U.S. Appl. No. 12/276,679.
Office Action Issued May 6, 2011 in U.S. Appl. No. 12/470,220.
Office Action issued Apr. 26, 2011 in JP Application No. 2007-556647.
Office Action issued Jun. 17, 2011 in U.S. Appl. No. 12/680,811.
Office Action issued Jul. 30, 2010 in Chinese Application No. 20068006138.6.
Office Action Issued Sep. 7, 2010 in Japanese Application No. 2007-553675.
Office Action issued Dec. 7, 2010 in U.S. Appl. No. 12/470,220.
International Preliminary Report on Patentability for the related International Application No. PCT/US2008/077352 dated Apr. 13, 2010.
Office Action issued Jul. 29, 2011 in U.S. Appl. No. 11/817,075.
Definition of "seal" as found on Merriam-Webster.com, retrieved Jul. 21, 2011.
Office Action Issued Oct. 6, 2011 in U.S. Appl. No. 10/545,160.
Chinese Office Action for the related Chinese Application No. 200680006138.6 dated Jun. 5, 2009.
International Search Report and Written Opinion for the related International Application No. PCT/GB2006/000528 dated May 22, 2006.
Chinese Office Action for the related Chinese Application No. 200680006138.6 dated Dec. 11, 2009.
Office Action for the related U.S. Appl. No. 11/817,075 dated Dec. 21, 2009.
Japanese Office Action for the related Japanese Application No. 2006-502257 mailed Jan. 15, 2010.
Office Action for the related U.S. Appl. No. 10/545,160 dated Mar. 3, 2010.
Office Action for the related U.S. Appl. No. 11/817,075 dated Aug. 27, 2008.
Office Action for the related U.S. Appl. No. 11/817,075 dated Feb. 20, 2009.
Office Action for the related U.S. Appl. No. 11/817,075 dated Jul. 28, 2009.
International Search Report for the related International Application No. PCT/US2008/077352 mailed Jan. 30, 2009.
Office Action issued Sep. 23, 2011 in CN Application No. 200880110889.1.
Office Action issued Nov. 18, 2011 in U.S. Appl. No. 11/817,075.
Office Action issued Dec. 23, 2011 in U.S. Appl. No. 12/276,679.
Office Action issued Jan. 5, 2012 in U.S. Appl. No. 12/680,811.
Witness statement of T. E. Weston (inventor), Aug. 27, 2010.
Second witness statement of T. E. Weston (inventor), Mar. 24, 2011.
Third witness statement of T. E. Weston (inventor), Jan. 5, 2012.
Witness statement of John Davison, May 3, 2011.
Statement from claimant in UK revocation proceeding regarding EP Patent No. 1558311, Jul. 15, 2010.
Defendant's counter-statement in UK revocation proceeding regarding EP Patent No. 1558311, Aug. 31, 2010.
Defendant's supplementary counter-statement in UK revocation proceeding regarding EP Patent No. 1558311, Mar. 25, 2011.
Written Preliminary Evaluation in UK revocation proceeding regarding EP Patent No. 1558311, Nov. 10, 2011.

Witness statement of Barry Peter Liversidge on behalf of tip-top.com Ltd. in UK revocation proceeding regarding EP Patent No. 1558311, Jan. 19, 2012.

Defendant's further counter-statement in UK revocation proceeding regarding EP Patent No. 1558311, Jan. 17, 2012.

Defendant's consolidated counter-statement in UK revocation proceeding regarding EP Patent No. 1558311, Mar. 9, 2012.

* cited by examiner

SAFETY NEEDLE

CROSS-REFERENCE TO RELATED APPLICATIONS

This application is a Section 371 of International Application No. PCT/GB2005/000357, filed Feb. 3, 2005, which was published in the English language on Aug. 10, 2006, under International Publication No. WO 2006/082350 A1 and the disclosure of which is incorporated herein by reference.

BACKGROUND OF THE INVENTION

This invention relates to a safety needle and in particular to safety needle pack.

Needle stick injuries carry a significant risk of spreading infection, such as HIV and hepatitis, and are commonplace among healthcare workers. The USA has led the way in introducing legislation that obliges healthcare providers to use the safest devices when giving injections, intravenous drug administration and similar invasive procedures. Other countries are following and, even without legislation, the ever-present risk of litigation has alerted pharmaceutical companies and health authorities to seek suitable safe devices.

As a result of the heightened awareness of needle stick injuries, there have been a large number of inventions addressing this issue, some more successful than others. Most take the form of a protective sleeve which covers the needle tip after the injection has been given, or means for retracting the needle rapidly into the syringe barrel. Such a safety needles are exemplified by U.S. Pat. No. 4,911,693, U.S. Pat. No. 4,813,940 and U.S. Pat. No. 5,104,384.

A common requirement for drug administration is to draw the drug from a vial or bulk container, or first reconstitute a lyophilised drug, and then draw up the required volume of drug from the reconstitution vessel. Good practice demands that separate needles are used for such procedures, to avoid contamination and "coring" of the rubber vial closure, and from a practical viewpoint, the needle used to draw up the drug usually will be larger than the delivery needle.

Often it is required for the needle tip to be visible prior to giving the injection because frequently a small amount of drug must be aspirated to clear out trapped air, and to correct the volume after drawing up the drug from a bulk container. Also, two of the most common types of injection given are intradermal and intravenous, and both require that the needle tip be visible to ensure that the tip is inserted into the tissues or vein bevel-side up.

It is particularly problematic to provide a low-cost needle which is able to prevent needle stick injuries, whilst allowing the tip of the needle to be visible during injection. At present there are no such devices on the market. There is therefore a need for a low cost safety needle which prevents needle stick injuries in healthcare workers but allows the tip of the needle to be exposed.

BRIEF SUMMARY OF THE INVENTION

Accordingly, the present invention provides a safety needle comprising a hollow needle, a needle hub surrounding the hollow needle, a slidable sleeve slidably mounted on the needle hub and a pack surrounding the hollow needle, needle hub and slidable sleeve, the needle hub, the slidable sleeve and the pack having a first (receiving) end which is proximal to (i.e. furthest from) the tip of the needle and a second (injection) end which is proximate to (i.e. nearest to) the tip of the needle (or distal end), wherein the receiving end of the needle hub is suitable for connection to an injection device and the slidable sleeve is adapted to slide in the direction of the length of the needle between an extended position in which the injection end of the needle is located inside the slidable sleeve and a retracted position in which the injection end of the needle projects from the slidable sleeve, via an intermediate position between the extended position and the retracted position in which the injection end of the needle projects partially from the slidable sleeve, such that, in use, the slidable sleeve is moved in to the intermediate position for injection in to a patient and then as the needle is inserted into a patient, the slidable sleeve is caused to move into the retracted position, and in moving in to the retracted position a resultant (or restoring) force is generated such that on removal of the needle from the patient the resultant force causes the slidable sleeve to move towards the injection end of the needle hub and into the extended position, the safety needle further comprising a locking mechanism capable of retaining the slidable sleeve in an extended position after removal of the needle from the patient, and wherein the pack is releasably mounted on the needle hub and slidable sleeve such that the injection end of the pack covers at least the injection end of needle and the receiving end of the pack has an open portion to expose the receiving end of the needle hub, and by causing the pack to be moved in a direction towards the receiving end of the needle hub, the pack engages with the slidable sleeve which is retracted from the extended position to the intermediate position.

This safety needle pack protects the user from needle stick injuries while the safety accessory, namely the needle hub and the slidable sleeve, are primed for use. By priming the safety accessory for use, the slidable sleeve is caused to move in to an intermediate position between the extended and retracted positions such that the needle bevel is exposed.

The present invention also provides a method for priming an injection device comprising the steps of inserting an injection device in to the receiving end of the needle hub of the safety needle pack as claimed in any preceding claim, moving the pack towards the injection device such that the slidable sleeve moves in to the intermediate position, and removing the pack.

The present invention further provides a method for injecting a patient using the safety needle pack as defined above.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

In the drawings, like parts are given the same reference numerals.

The applicants have found that the process of exposing the tip of the needle can, in itself lead to needle stick injuries. This is particularly undesirable where the user is injecting cytotoxic agents, for example during cancer chemotherapy. The safety needle pack of the present invention avoids such injuries by providing a pack which shields the user from the needle tip whilst the tip of the needle is being exposed, at least partially. By at least partially, means that the tip of the needle is not exposed to the extent that it is exposed when the user injects the needle through the skin of the patient but is exposed sufficiently for the user to see the bevel of the needle, in order to guide the tip in to a specific part of the patient or to aspirate air or expel any excess drug. When the needle tip is at least partially exposed the arrangement of the slidable sleeve and the needle hub hold the slidable sleeve in this intermediate position.

Figure 1:
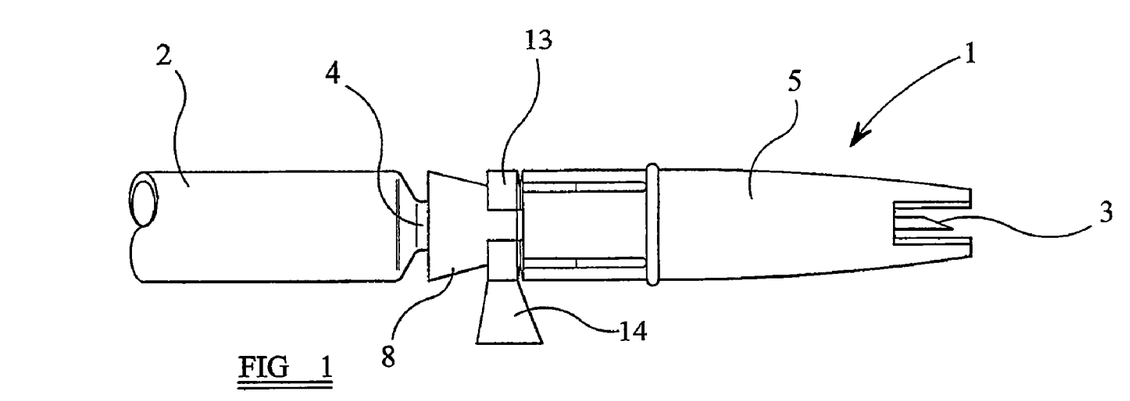
FIG. 1 shows a safety needle attached to a syringe without the pack.

FIGS. 1-8 exemplify a safety needle for preventing needle stick injuries which is suitable for use with the pack of the present invention. FIG. 1 shows the general arrangement of a safety needle 1 (i.e. the safety needle accessory and the needle 3) of the type which may be used with the present invention as fitted to a male Luer taper connector 4 of syringe 2, with the end of the hollow (e.g. hypodermic) needle 3 enclosed by the slidable sleeve 5. The slidable sleeve 5 is prevented from longitudinal movement on the needle hub 7 by a locking ring 13, which may be removed by pulling on the tab 14. The removable locking ring may be connected to the needle hub and/or the slidable sleeve. Although embodied in the Figures as cylindrical, the cylindrical shape of the needle hub and slidable sleeve may be replaced by triangular, rectangular or other shapes to suit the application.

Figure 2:
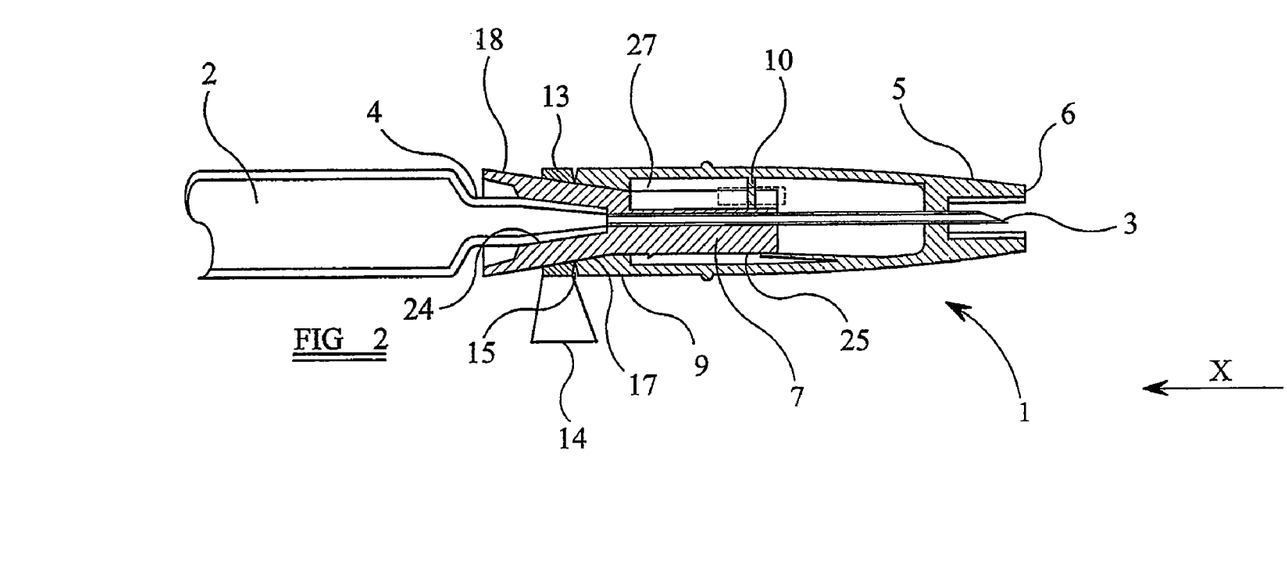
FIG. 2 shows a centre line cross-section through the safety needle attached to a syringe.
Figure 3:
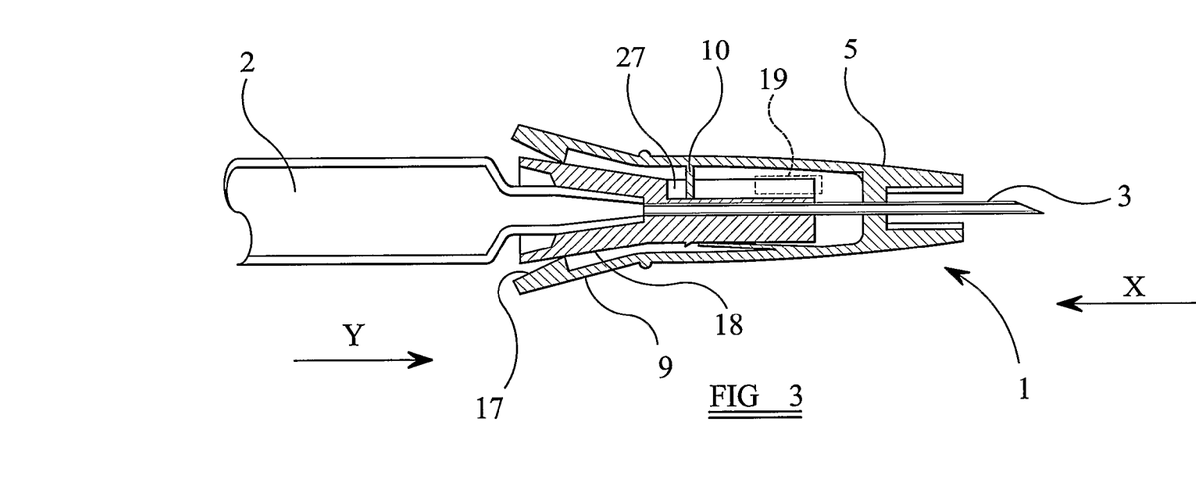
FIG. 3 shows the slidable sleeve partly retracted to expose the hollow needle.

FIG. 2 is a cross-section through the axis of the safety needle 1. The needle hub 7 is cylindrical and terminates at the end which receives the syringe with a conical section 8, and is moulded onto the needle 3. The conical section 8 has an inner female Luer cone 24 which is shown frictionally attached to the male Luer cone 4 of syringe 2 (the Luer system for attaching the needle to the syringe has two main forms, that is a taper friction fit and a screw thread and both are included in the present invention). The cylindrical slidable sleeve 5 shrouds the needle 3 and the needle hub 7, and is freely sliding on and guided by the needle hub 7. At the receiving end (i.e. the end which receives the syringe) of slidable sleeve 5, there are four cantilever arms 9 which bear resiliently upon the surface 18 of the conical section 8. The slidable sleeve 5 is free to slide on the needle hub 7, but is temporarily prevented from doing so by the locking ring 13. Locking ring 13 is moulded integrally with the slidable sleeve 5 by a frangible joint 15, and may be partially or wholly detached by pulling on the tab 14 to break the frangible joint 15. It is preferred that the ring 13 remains attached to the slidable sleeve 5 to reduce the number of discarded parts. In addition, the frangible joint provides a tamper-evident lock. Alternatively, the locking ring 13 may be moulded to the needle hub 7 via a suitable frangible connection. When the locking ring 15 is removed, as shown in FIG. 3 the slidable sleeve 5 may be pushed in the direction of arrow X by acting on the face 6, when it will move relative to the needle hub 7 to expose the needle 3. As the slidable sleeve 5 moves, the cantilever arms 9 are forced outwards by the surface 18 of the conical section 8. The cantilever arms 9 are resilient and the reaction force against the surface 18 produce a resultant force Y acting against arrow X, so that when the original force is removed, the slidable sleeve 5 returns to cover the tip of needle 3.

Since the resultant force is provided by the slidable sleeve 5 itself, no separate spring, e.g. a helical spring, is required in this embodiment although a separate spring could be used if desired. Thus, the resultant force may be generated within the slidable sleeve, for example by the sleeve having an elastically deformable portion, and/or by the accessory further comprising an elastically deformable member, such as a spring.

Figure 6:
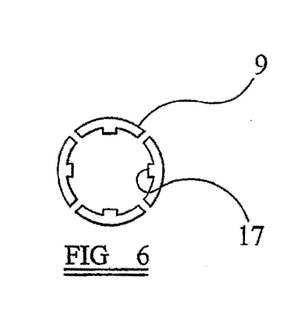
FIG. 6 shows the receiving end of the slidable sleeve showing the cantilever arms.

As shown in FIG. 6, the cantilever arms 9 may have pads 17 which bear onto the surface 18 and, by suitably designing the bearing surfaces of the pads 17, various spring characteristics may be obtained. Although four cantilever arms 9 are shown, any number could be employed. At least one cantilever arm 9 is required for this embodiment although 2 to 6 are preferred and particularly preferably four.

Figure 8:
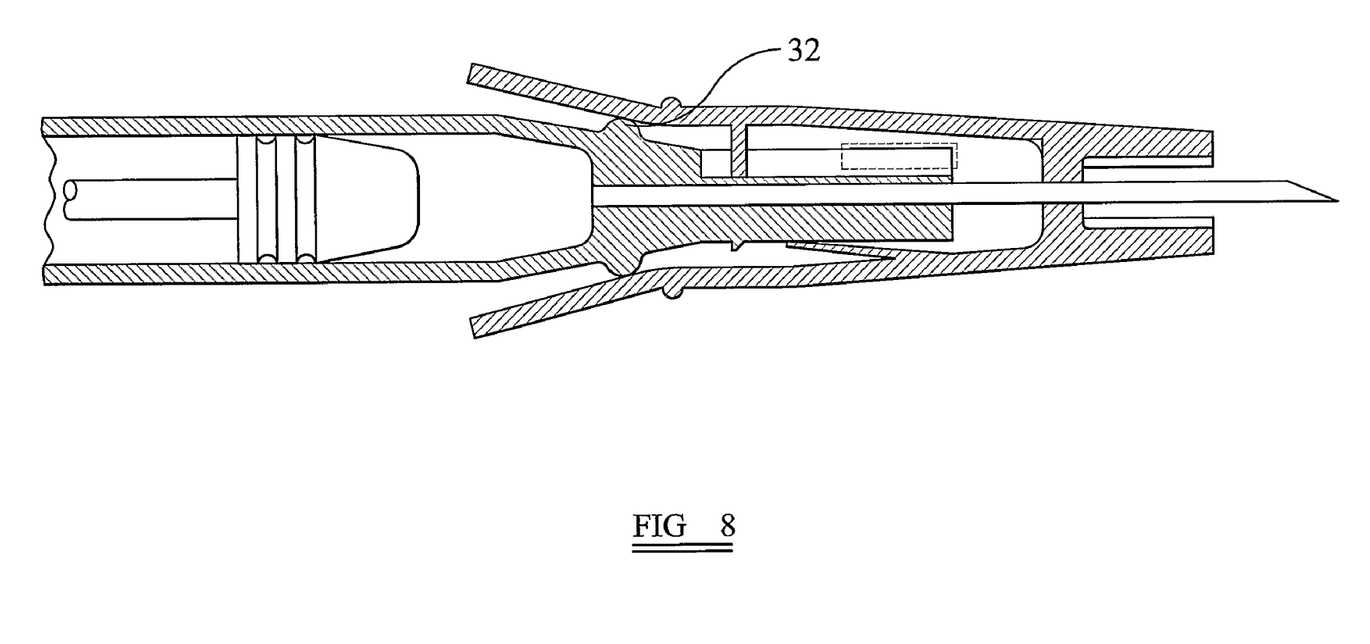
FIG. 8 shows an integral syringe barrel and needle hub.

Although the surface 18 is exemplified by a conical surface, other embodiments may be used within the scope of the present invention. In the Figures, the surface is straight, i.e. substantially conical by which the applicant means sufficiently conical to generate a resultant force, however, the surface need not be straight as shown, but may be curved to give a more linear return rate. Thus the force Y could be substantially constant over a reasonable working stroke of the slidable sleeve 5. In addition, the whole surface 18 of the receiving end of the needle hub 17 need not be conical. In fact just one tapered section, e.g. a tapered ridge, would be sufficient. The tapered section does not have to project from the surface of the needle hub 7. The tapered section could also descend into the wall of the needle hub, i.e. a tapered detent rather than a tapered ridge. Also, as described below with reference to FIG. 8, provided the slidable sleeve 5 is suitably configured, a projection in the surface 18 of the needle hub 7 will suffice.

These different arrangements provide a great deal of design flexibility in the safety needle accessory of the present invention. For example, the linearity of the return rate may be varied depending on the particular requirements for a particular application.

Figure 4:
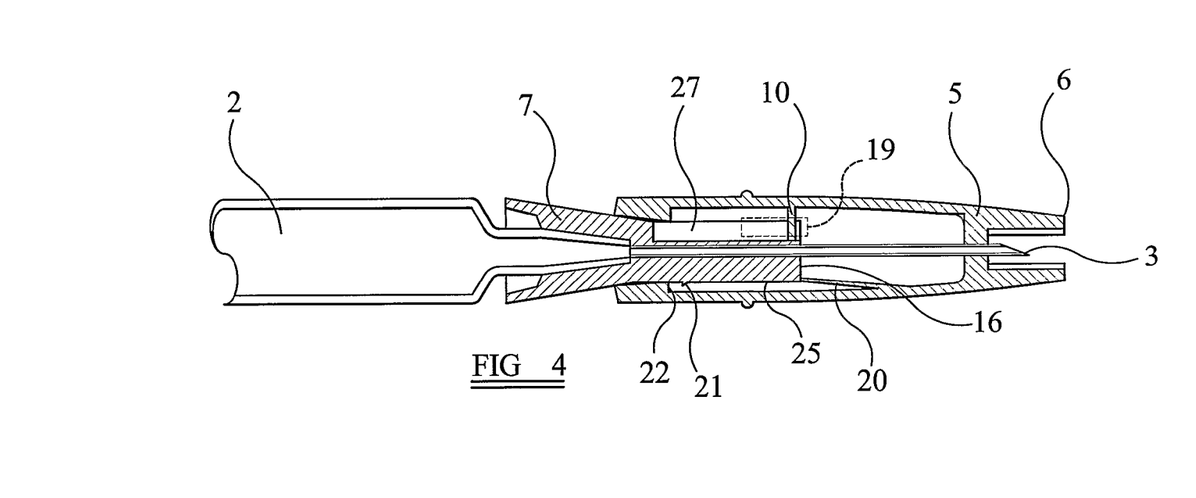
FIG. 4 shows a safety needle with the slidable sleeve in an extended and locked position.

Referring to FIG. 4, when the slidable sleeve 5 returns in direction Y, it travels slightly past its original staring position, so that the resilient pawl 20 which was depressed by the surface 25 of hub 7, snaps out to act against face 16 of hub 7. This ensures that the slidable sleeve 5 cannot be pushed back towards the syringe 2, and therefore the needle 3 is safely covered. It is preferred that there is a pre-load between the cantilever arms 9 and hub 7 to ensure that the slidable sleeve 5 is sufficiently biased in the direction of arrow Y to complete its full displacement potential.

Figure 5:
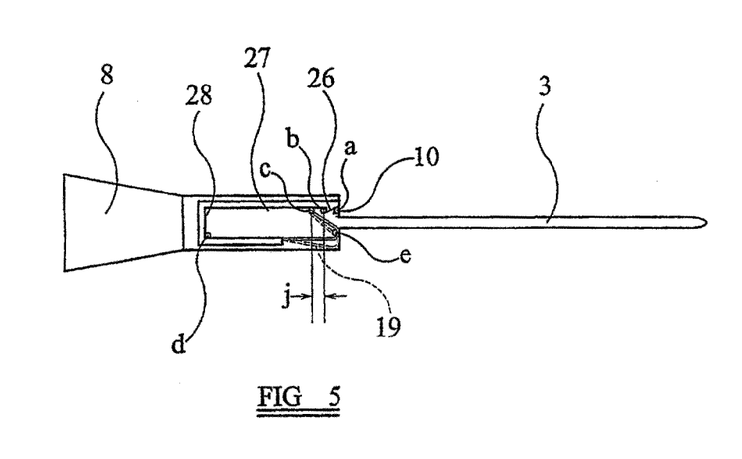
FIG. 5 shows the detent mechanism.

The slidable sleeve preferably has a first extended position where the slidable sleeve is able to be moved towards the receiving end of the needle hub and a second extended position where the slidable sleeve is in a locked position. The different start and finish positions of the slidable sleeve 5 is achieved by a detent mechanism shown in FIG. 5, which is to be read in conjunction with FIGS. 2, 3 and 4. After the first two or three millimetres of movement, a detent integral with the slidable sleeve "switches" so that the return of the slidable sleeve trips a latching pawl, so that the slidable sleeve returns only to the "safe" position; that is the pawl prevents the slidable sleeve from being moved towards the syringe a second time, and thus protects the tip of the needle. As part of the detent mechanism, an inside surface of the slidable sleeve has a pin 10 which engages a sprag 26 and a resilient pawl 19 attached to the needle hub 7 thereby holding the slidable sleeve in the first extended position and, in use, allowing the slidable sleeve to move into the second extended position. Pin 10 is integral or attached to the slidable sleeve 5. Sprag 26, resilient pawl 19, and recess 27 are moulded integrally with the needle hubs 7, 8, and the pin 10 extends into the recess, and allowed to move freely except where controlled by the detent and the boundaries of the recess. In the initial assembly of the safety needle, the slidable sleeve 5 is placed over the needle 3 with pin 10 proximate to the sprag 26 (formed as part of the needle hub 7) at position a (FIG. 5). As the slidable sleeve 5 is moved further, the pin 5 deflects the resilient pawl 19, until the pin 10 is trapped behind sprag 26 at position b. In this position the slidable sleeve 5 is trapped on the needle hubs 7, 8 and cannot be removed without applying considerable force. This is the position of the components as supplied to the end user, and the location of the locking ring 13 takes account of this. With the locking ring 13 removed, the slidable sleeve 5 is pushed further towards the syringe 2, and pin 10 again deflects the resilient pawl 19 until the pin 10 reaches position c. This distance j defines the initial displacement of the slidable sleeve 5, when starting the injection, and the tip of needle 3 may be level with the face 6 of slidable sleeve 5. The slidable sleeve 5 may now be moved towards the syringe until the pin 10 reaches the end wall 28 of the recess 27 at position d. This position defines the maximum displacement of slidable sleeve 5, and thus the maximum exposure of the needle 3. At any time the force acting on slidable sleeve 5 is removed, the slidable sleeve 5 will return in the direction of arrow Y until pin 10 reaches the position e. Pin 10 would also help prevent the removal of slidable sleeve 5, but additionally the tooth 21 is now proximate to face 22 on a cantilever arm 9, which prevents the removal of the slidable sleeve 5. In this final position, pawl 20 engages with face 16 of hub 7 and prevents the slidable sleeve 5 from being moved. It should be noted that with the present diagrammatic presentation of the safety needle, a small amount of rotational movement is necessary between the slidable sleeve 5 and hub 7 to permit the pin 10 to move from position c to position e, but the rotation is preferably negligible.

The detent mechanism is interchangeable between the slidable sleeve 5 and needle hub 7 if required. Also, the detent mechanism described hereinabove is but one of a number of such mechanisms, the main requirement being to permit the following sequence of operation: permit the slidable sleeve to be moved sufficiently so that the opening in the slidable sleeve is level with or just in front of the needle tip, at which position the detent must be activated so that if the displacing force on the slidable sleeve is removed, the slidable sleeve slides forward and locks, thus protecting the user from contact with the needle tip. Typically, the tip of the needle would be about 3 mm back from the face of the opening in the slidable sleeve at the start, and 1 mm back from the face when the detent is activated.

Figure 7:
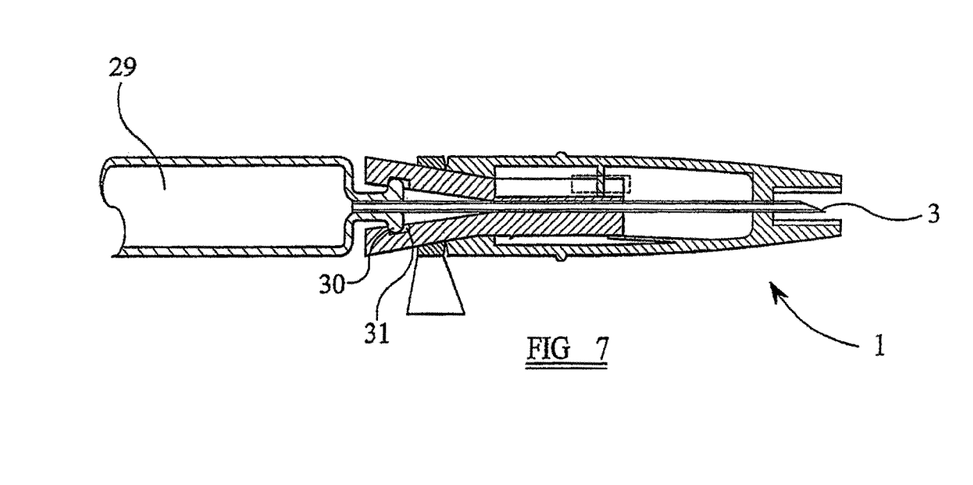
FIG. 7 shows the barrel of a typical glass syringe used commonly for pre-filling with a drug, assembled with a safety needle.

FIG. 7 shows the device 1 as previously described, except that in this embodiment the needle 3 is bonded into the outlet end of the syringe barrel 29. The needle is free to pass through the needle hub 7, and the cone 9 is adapted at 31 to snap-fit over the projection 30. The form of projection 30 is produced as a result of rolling the glass onto a mandrel, whereby the excess glass is forced in to the shape as shown. Alternatively, a more defined snap-fitting termination may be formed, the object being to make the device 1 difficult to remove after assembling it to the syringe barrel.

FIG. 8 shows a safety needle 1 in which the needle hub 7 is integral with the barrel of the syringe 2. The slidable sleeve 5 is then attached to the needle hub 7 in the manner as described hereinbelow. The material of the needle hub 7, which also constitutes the barrel of the syringe, would, of course, have to be made from a drug-compatible material.

As mentioned hereinabove, FIG. 8 also shows the separate feature of the projection 32 on the surface 18 of the needle hub 7 which may be used to deflect the slidable sleeve 5 thereby generating the resultant force. This embodiment, i.e. incorporating the projection 32, provides a highly non-linear return rate since the length of the slidable sleeve 5 is effectively reduced as the slidable sleeve 5 and the needle hub 7 are slid together, thereby increasing the stiffness of the slidable sleeve 5.

As an alternative to the tapered outer surface of the needle hub 7, the slidable sleeve has at least one cantilever arm which engages a helical track in the outer surface of the needle hub such that, in use, as the needle is inserted into a patient, the at least one cantilever arm is displaced radially by the helical track in the outer surface of the needle hub thereby generating the resultant force. Thus, as the slidable sleeve 5 is caused to move towards the receiving end of the needle hub 7, one or more cantilever arms 9 are forced to follow the direction of the helical tracks. Since the cantilever arms 9 are resilient, a resultant force will be generated.

As an alternative to cantilever arms, the receiving end of the slidable sleeve itself may have elastic properties such that, in use, as the needle is inserted into a patient, the resultant force is generated within the slidable sleeve. By elastic properties the applicant means that the resultant force is generated within a radially continuous slidable sleeve, i.e. a sleeve without cantilever arms. The elastic properties may be achieved by using an elastic material, such as an elastomeric polymer. Alternatively, the receiving end of the slidable sleeve may be concertinaed, with the ridges, of course, running parallel to the hollow needle. The elastic properties could also be generated using a circumambient spring attached to the slidable sleeve.

As a further alternative, instead of the resultant force being generated in the slidable sleeve 5 itself, the safety needle may incorporate an alternative, or additional, resultant mechanism, such as a helical spring. Such safety needles are exemplified in U.S. Pat. No. 4,911,693, U.S. Pat. No. 4,813,940 and U.S. Pat. No. 5,104,384.

FIGS. 9-14a show an embodiment of the present invention in which the needle hub and the slidable sleeve are adapted to allow the slidable sleeve to be retracted into and held at an intermediate position between the extended position and the retracted position such that, in use, the tip of the needle 2 projects partially from the slidable sleeve, that is the needle bevel is exposed. In this intermediate position the locking mechanism is not engaged and hence the slidable sleeve may be retracted further into the (fully) retracted position as it is inserted into the patient. The advantages of this arrangement are that exposing the tip of the needle partially allows the user to position the needle more precisely on, for example, the patient's skin, and also facilitates the aspiration of trapped air and excess drug. The use of the pack prevents needle stick injuries when the safety needle is in the intermediate position.

Figure 9:
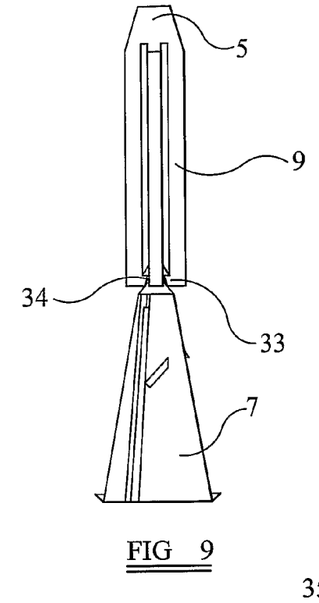
FIG. 9 shows a safety needle as assembled by the manufacturer, prior to inserting it into its pack.
Figure 9A:
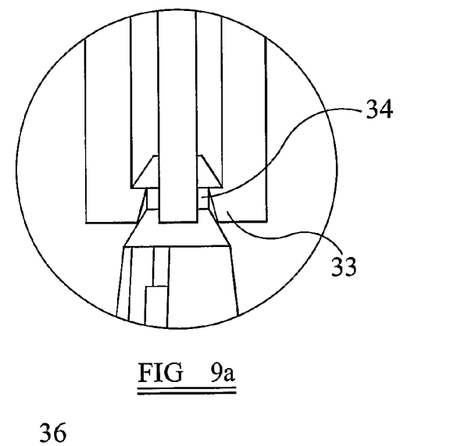
FIG. 9a is an enlarged view of the engagement of the slidable sleeve to the needle hub of the safety needle of FIG. 9.
Figure 10:
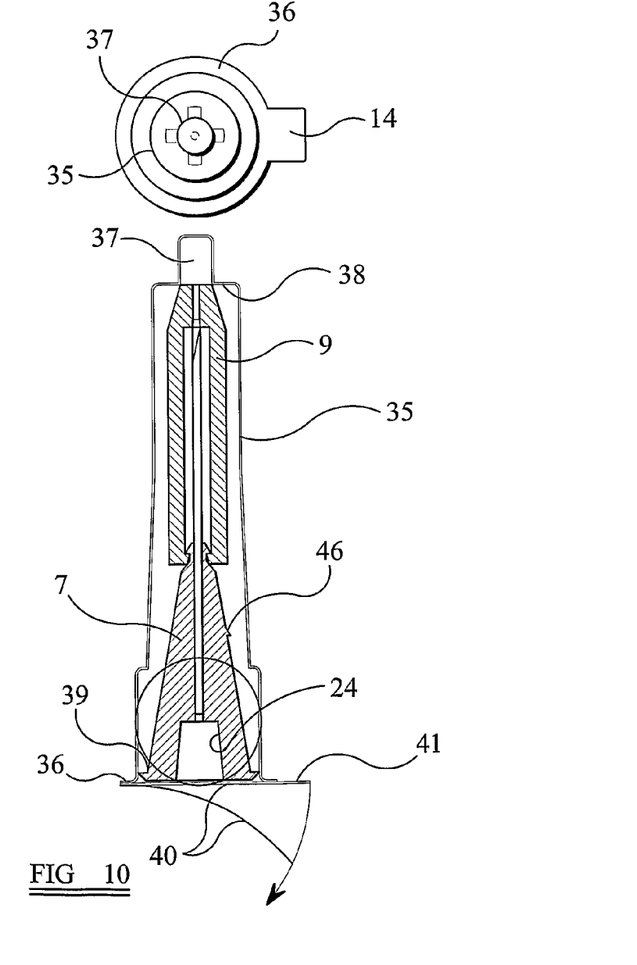
FIG. 10 is a centre-line section of the safety needle in its pack.

FIG. 9 shows the device as assembled by the manufacturer, and comprises a needle hub 7, being of conical or other tapering form. Slidable sleeve 5 has cantilever arms 9 attached or integral, the arms terminating with a projection 33, which engages with undercut 34 of the needle hub 7, shown in greater detail in FIG. 9a. In the position shown, there is little load on the spring cantilever arms 9, but sufficient to hold the components together. Referring to FIG. 10, this is a centre-line cross-section through the safety needle assembled into its pack 35. Pack 35 is releasably mounted on the needle hub and slidable sleeve, that is the accessory is held within the pack 35, for example by friction, but may be removed by the user. To facilitate the releasable mounting the pack and accessory have engageable portions which may simply be the surfaces of the pack and accessory. These surfaces may be textured or have projections. The pack 35 preferably tubular and also preferably made from a deep-drawn vacuum formed plastics material. The pack 35 is shown with a flange 36 and open at the receiving end of the needle hub 7, and closed at the injection end by the extension 37. The inner face of shoulder 38 rests on the end face of the slidable sleeve 5. The needle hub 7 has one or more projections 39, which provide a light frictional retaining force on the inside of the pack 35 to prevent the safety needle from falling out. The safety needle may be further retained inside the pack 35 by a releasable (peel-off) membrane 40, which is preferably gas permeable. The membrane 40 is bonded to flange 36, and may be made from a porous material such as TYVEK® brand spunbonded olefin i.e., a spun-bonded high-density polyethylene available from DuPont and which is used extensively in pharmaceutical packaging to permit a sterilizing gas, such as ethylene oxide, to penetrate the pack whilst preventing ingress of bacteria during storage. Other peelable materials may be used according to the sterilization process used. The membrane 40 may have a tag 41 to assist removal. The needle hub 7 has a syringe adaptor 24 which may be configured to suit the common Luer taper or threaded Luer lock syringe nozzles.

Figure 11:
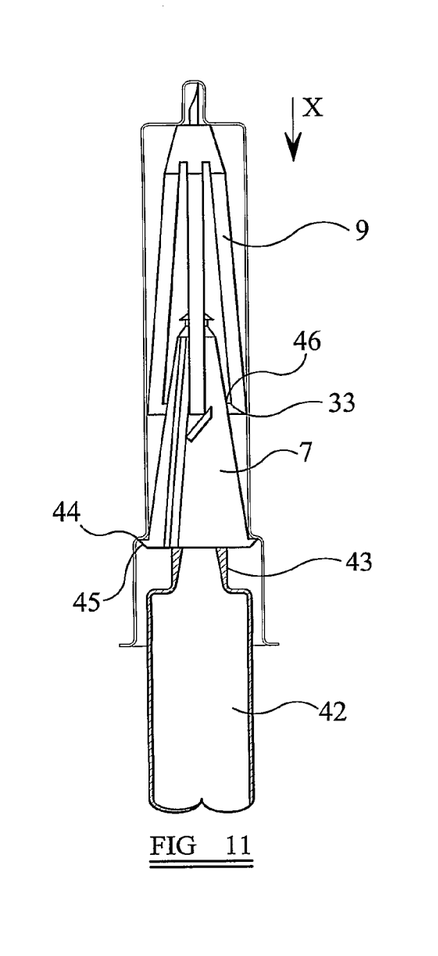
FIG. 11 shows how the pack is used to hold the safety needle when connecting it to a syringe.
Figure 12:
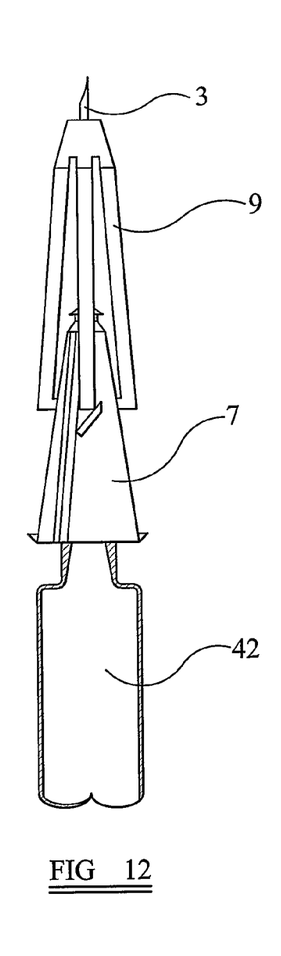
FIG. 12 shows the safety needle after removing the pack, and ready to use.
Figure 12A:
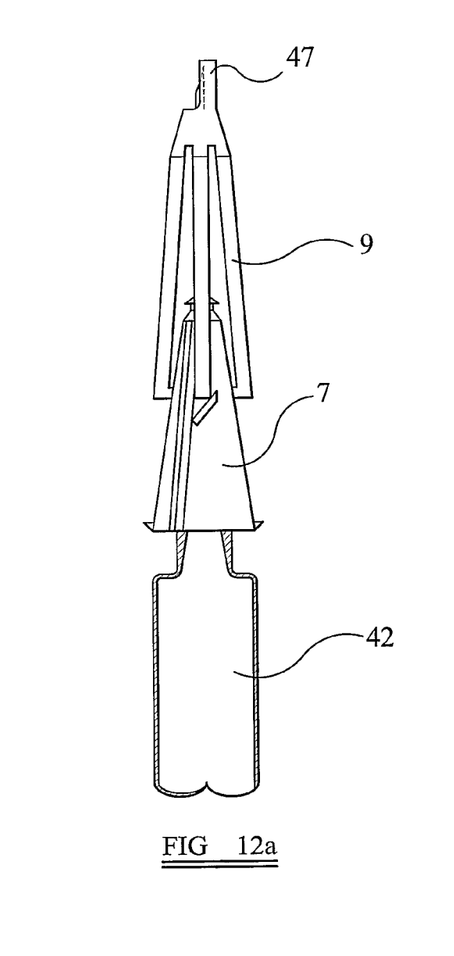
FIG. 12a shows an alternative shroud to increase the protection against needle stick injuries, whilst allowing the needle bevel to be seen immediately prior to giving the injection.

Referring to FIG. 11, to assemble the safety needle to a pre-filled syringe 42, the user removes the peelable membrane 40 by pulling on tag 41. Holding the pack 35, the user pushes the adaptor 24 of the needle hub 7 in the direction of the arrow X onto the syringe connector 43. This causes the inner face of the shoulders 38 to press against face of slidable sleeve 5 which moves towards the syringe. The injection end of the pack 35 has an extended portion which is capable of housing the tip of the needle 3 in the intermediate position and the shoulders 38 of the extended portion abut against the injection end of the slidable sleeve thereby causing the slidable sleeve 5 to move in to the intermediate position when the pack 35 is caused to move towards the receiving end of the needle hub 7. At the same time, the cantilever arms 9 are forced outwards as they travel up the surface of the needle hub 7, until the small shoulder 44 on the slidable sleeve 5 reaches the projection 45 on the needle hub 7, thus preventing further movement. At or about this point, at least one of the projections 33 snaps over a catch 46 on the needle hub 7. The cantilever arms 9 are now loaded radially, and exerting a resultant force urging the slidable sleeve 5 off the needle hub 7. The pack 35 may now be removed, and catch 46 prevents the slidable sleeve 5 from coming off the needle hub 7 through the resultant force of the cantilever arms 9. With pack 35 removed, the safety needle will appear as shown in FIG. 12, and is ready for use. The tip needle 3 is thus partially exposed, i.e. the bevel of the needle may be seen by the user projecting from the slidable sleeve 5, and the user may aspirate trapped air and excess drug. FIG. 12a shows the safety needle ready for use, as in FIG. 12, but with an extension 47 on face of slidable sleeve 5 extended to shroud partly the tip of the needle 3, which will afford more protection, but make aspiration of air and excess drug slightly more difficult.

Figure 13:
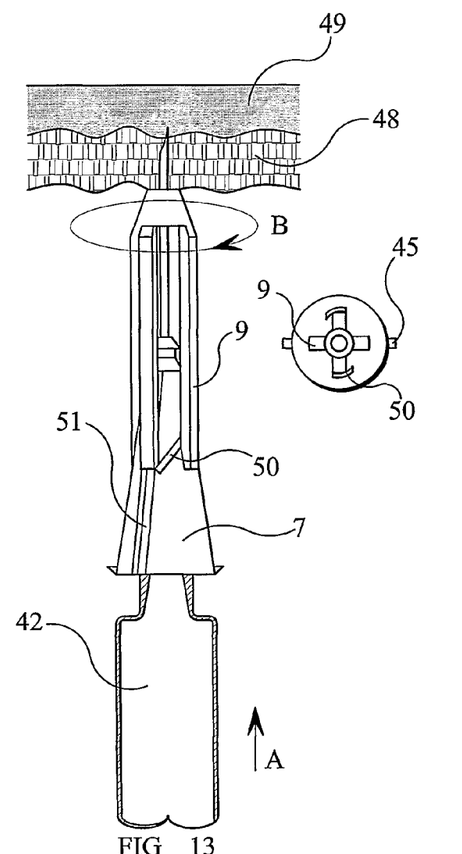
FIG. 13 shows the safety needle being used to inject medicament.
Figure 14:
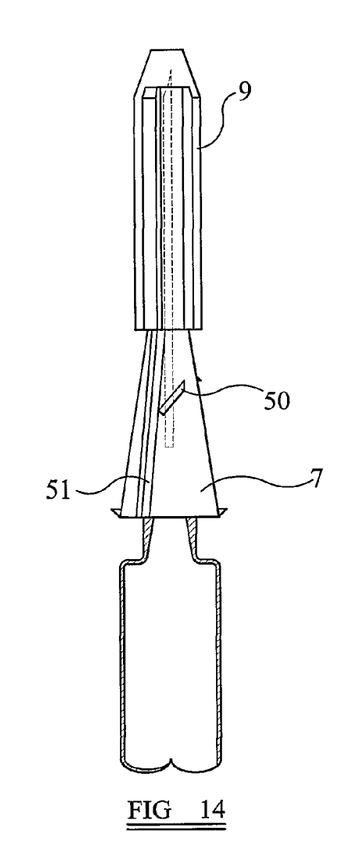
FIG. 14 shows the safety needle after the injection with the protective slidable sleeve locked in a forward position to cover the needle tip.
Figure 14A:
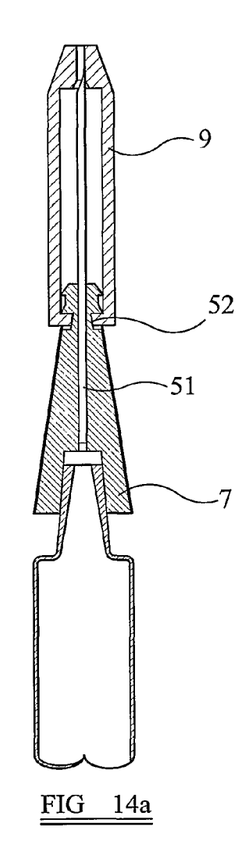
FIG. 14a shows a centre-line section through the safety needle, rotated to show the part of the locking mechanism.

Referring to FIG. 13, the user pushes the needle 3 in the direction of arrow A through the patient's epidermis 48 and into the subcutaneous tissue 49, which brings the face of the slidable sleeve 5 into contact with the stratum corneum of the patient's epidermis 48. Further movement in the direction of arrow A pushes the slidable sleeve 5 towards the syringe 42, and thus the cantilever arms 9 are forced further outwards by the conical surface of the needle hub 7. At the same time, the end of at least one cantilever arm 9 is forced against a cam 50 which causes the slidable sleeve 5 and cantilever arms 9 to rotate in the direction of arrow B, until the end of cantilever arm 9 drops into the groove 51. Groove 51 has a slope towards the needle, which maintains the resultant force of the cantilever arm 9. At this point, (which represents only a millimetre or two of movement of the slidable sleeve 5), if the safety needle is withdrawn from the patient, the resultant force of the cantilever arms 9 urges the slidable sleeve 5 towards the tip of the needle 3 until the tip of the needle 3 is shielded by the slidable sleeve 5. At the end of travel of the projection 33 and the cantilever arm 9, the projection 33 on cantilever arm 9, which is still sliding in the groove 51, drops into the hole 52. This locks the slidable sleeve 5 in position and prevents the slidable sleeve 5 being pushed back towards the syringe 42, or being pulled off the needle hub 7. This position is shown in FIGS. 14 and 14a, the latter being a section through the centre-line, and the safety needle rotated to show the grooves 51 and holes 52, with the projections 33 on cantilever arms 9 located within the holes 52. Although the lockably engaging projection 33 and hole 52 are shown with reference to cantilever arms 9, any slidable sleeve 5 may be locked into position using one or more projections 33 and corresponding one or more holes 52. Such an arrangement results in a less complex, and hence less costly, safety needle accessory and avoids introducing opposing frictional and/or detent forces which result from an integral but independent locking mechanism. An advantage of the projection 33/hole 52 mechanism is that the locking mechanism provides substantially no resistance against the resultant force as the slidable sleeve 5 moves from the retracted position to the extended position. When the slidable sleeve 5 reaches the extended position the locking mechanism engages which then resists the resultant force.

The protective pack 35 confers safe storage and handling advantages, allows the safety needle to be assembled to a syringe without risking premature operation of the safety mechanism, and does not add to the overall cost of the device, since it is similar to the vacuum-formed packs already in use for needles and syringes. For the user, the operation of the safety needle is practically identical to the use of a standard needle.

It is preferable that the coefficient of friction between the slidable sleeve 5 and the needle hub 7 is low, so that the resultant biasing force to return the slidable sleeve is not compromised by "stiction", or so high that the force required on the patient's skin to deflect the slidable sleeve 5 is excessive. This may be achieved by careful selection of materials. Such materials are known in the art, for example, the needle hub could be made from a high-density polyethylene or similar drug-compatible plastics material, and the slidable sleeve from an inexpensive plastics material such as polycarbonate, polystyrene, polyester or PVC. A more expensive, highly creep-resistant plastics material, for example polyphenylene sulfone, could also be used. As an alternative, the slidable sleeve, or just the at least one cantilever arm, may be made from metal, preferably stainless steel. The metal would be fabricated sufficiently thinly to provide the required elastic properties. If necessary, a lubricant may be used, or a lubricant may be incorporated with the polymers. Generally the materials should be suitable for sterilization by gamma radiation, but it is possible to select materials compatible with sterilization by steam or other gas such as ethylene oxide.

In a preferred embodiment, the slidable sleeve, prior to use, is not under any substantial load. Any substantial load indicates a load which is sufficient to cause the material of the slidable sleeve to undergo creepage during storage at ambient temperature.

Figure 15:
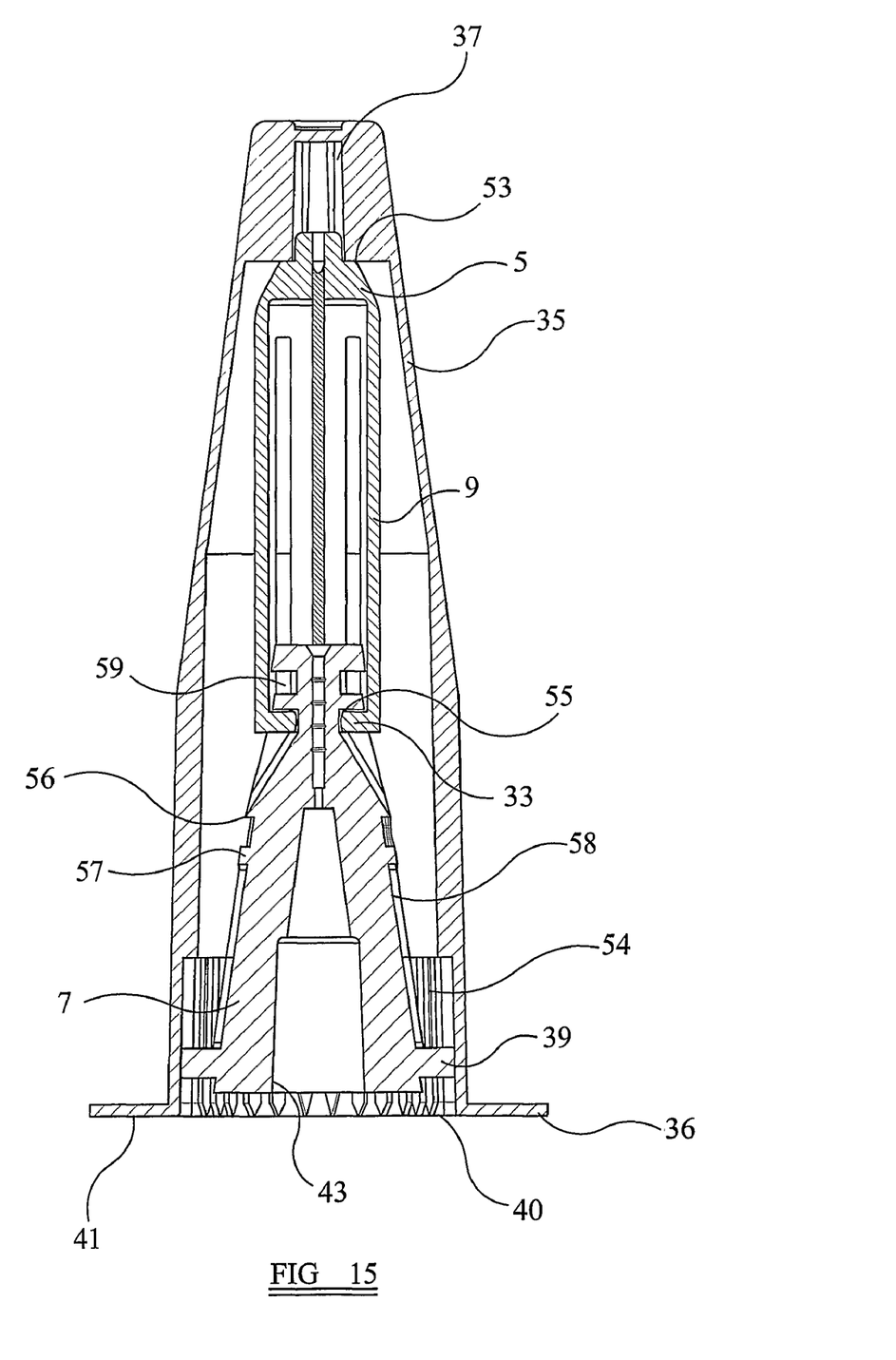
FIG. 15 shows a centre-line section of a further embodiment of the safety needle in its pack.
Figure 16:
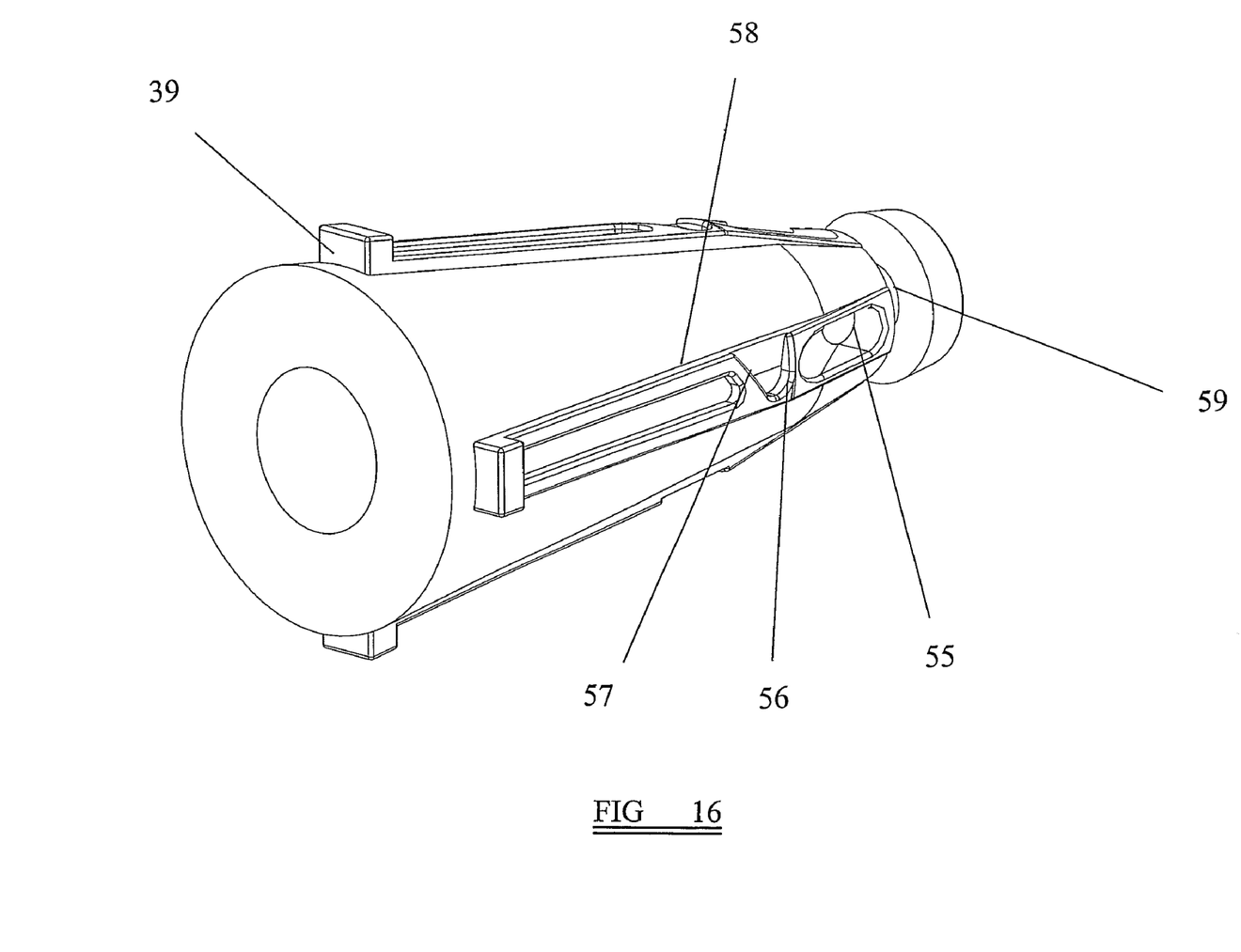
FIG. 16 shows a three-dimensional representation of the hub of the embodiment of FIG. 15.

FIGS. 15 and 16 show a further embodiment of the present invention in which the needle hub and the slidable sleeve are adapted to allow the slidable sleeve to be retracted into and held at an intermediate position while the needle is still contained within the pack. This embodiment further allows the accessory to be stored without any substantial load on the slidable sleeve 5 thereby preventing creepage during storage.

FIG. 15 shows a centre-line cross-section through the safety needle 1 assembled into its pack 35 and FIG. 16 shows a three-dimensional representation of the needle hub 7. Pack 35 is releasably mounted on the needle hub 7 and slidable sleeve 5. The pack 35 preferably tubular and also preferably made from a deep-drawn vacuum formed plastics material. The pack 35 is shown with a flange 36 and open at the receiving end of the needle hub 7, and closed at the injection end by the extension 37 defined by a plurality, e.g. six, ribs 53. The ribs 53 rest on the end face of the slidable sleeve 5. The needle hub 7 has one or more projections 39, which provide a light frictional retaining force on the inside of the pack 35 to prevent the safety needle from falling out. The pack 35 may also have a partially textured internal surface 54 which engages the projections 39 in order to prevent rotation of the accessory 1 within the pack. The safety needle may be further retained inside the pack 35 by a releasable (peel-off) membrane 40 as described hereinabove. The needle hub 7 has a syringe adaptor 24 which may be configured to suit the common Luer taper or threaded Luer lock syringe nozzles.

In the position shown in FIG. 15, the device is as assembled by the manufacturer. Slidable sleeve 5 has cantilever arms 9 attached or integral, the arms terminating with a projection 33, which engages with indent 55 of the needle hub 7. The indent 55 is of sufficient depth that the cantilever arms 9 are under substantially no load, i.e. the sleeve 5 is not radially expanded. In this position, the sleeve 5 is prevented from sliding off the needle hub 7 by the pack 35 and the engagement between the projection 33 on the cantilever arms 9 and the indent 55 on the hub 7.

To assemble the safety needle to a pre-filled syringe 42, the user removes the peelable membrane 40 by pulling on tag 41. Holding the pack 35, the user pushes the adaptor 24 of the needle hub 7 onto the syringe connector 43. This causes the inner face of the ribs 53 to press against face of slidable sleeve 5 which moves towards the syringe. The injection end of the pack 35 is capable of housing the tip of the needle 3 in the intermediate position. The ribs 53 of the pack 35 abut against the injection end of the slidable sleeve thereby causing the slidable sleeve 5 to move in to the intermediate position when the pack 35 is caused to move towards the receiving end of the needle hub 7. The indent 55 has a tapering interior surface which causes the sleeve to expand radially as the sleeve 5 is caused to move up the surface of the needle hub 7. The sleeve 5 is caused to move until the sleeve 5 is in the intermediate position wherein the needle tip is partially exposed. At or about this point, at least one of the projections 33 snaps over a catch 56 on the needle hub 7. The cantilever arms 9 are now loaded radially, and exerting a resultant force urging the slidable sleeve 5 off the needle hub 7. This resultant force is countered by the catch 56 on the hub 7. The pack 35 may now be removed, and catch 56 prevents the slidable sleeve 5 from coming off the needle hub 7 through the resultant force in the cantilever arms 9. With pack 35 removed, the safety needle is ready for use. The tip needle 3 is thus partially exposed, i.e. the bevel of the needle may be seen by the user projecting from the slidable sleeve 5, and the user may aspirate trapped air and excess drug.

The user pushes the needle 3 through the patient's epidermis and into the subcutaneous tissue, which brings the face of the slidable sleeve 5 into contact with the stratum corneum of the patient's epidermis. Further movement of the needle into the patient's skin pushes the slidable sleeve 5 towards the syringe 42, and thus the cantilever arms 9 are forced further outwards by the conical surface of the needle hub 7. At the same time, the end of at least one cantilever arm 9 is forced against a cam 57 which causes the slidable sleeve 5 and cantilever arms 9 to rotate (in an analogous manner to FIG. 14), until the end of cantilever arm 9 is directed along the guide 58. As shown in FIG. 16, the catch 56 and the cam 57 are preferably formed into a single structure. The projection 33 follows guide 58 as the sleeve is caused to retract. As the sleeve 5 retracts, the sleeve 5 is deflected radially by the sloping of the hub 7 towards the needle.

At this point, (which represents only a millimetre or two of movement of the slidable sleeve 5), if the safety needle is withdrawn from the patient, the resultant force of the cantilever arms 9 urges the slidable sleeve 5 towards the tip of the needle 3 until the tip of the needle 3 is shielded by the slidable sleeve 5. At the end of travel of the projection 33 and the cantilever arm 9, the projection 33 on cantilever arm 9, which is still following the guide 57, drops into the hole 59. This locks the slidable sleeve 5 in position and prevents the slidable sleeve 5 being pushed back towards the syringe 42, or being pulled off the needle hub 7.

The hole 59 is shown further towards the injection end of the hub 7 than the indent 55. This allows the hole 59 to be a circumferentially continuous hole which permits free rotation of the sleeve 5 around the hub in the locked position. This free rotation provides a more secure locked position. In a simple hole/projection arrangement, accidental rotation of the sleeve 5 might distort the sleeve sufficiently to disengage the hole and projection. Allowing free rotation means that the rotation is not resisted preserving the integrity of the locking mechanism.

As previously mentioned hereinabove, the syringe may be supplied empty or pre-filled. When a pre-filled syringe is used, the syringe is preferably sealed using a sealing cap or plug to prevent evaporation or loss of the drug, excipient, carrier and/or diluent by, for example, thermal expansion.

As well as application to a syringe, the same safety needle accessory described herein could form the basis of a intravenous giving set, so that the insertion of the needle into the patient's vein is simple and safe. Indeed, the safety needle accessory of the present invention may be used with any suitable injection device.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A safety needle comprising:
   a hollow needle having a tip for injecting into a patient,
   a needle hub that includes a catch and wherein the needle hub surrounds the hollow needle,
   a slidable sleeve that includes a projection and wherein the slidable sleeve is slidably mounted on the needle hub and slidable along the needle hub, and
   a pack surrounding the hollow needle, the needle hub and the slidable sleeve in a storage position and wherein the pack is releasably secured on at least one of the needle hub and the slidable sleeve by friction,
   the needle hub, the slidable sleeve and the pack each having a receiving end and an injection end distal to the receiving end,
   wherein the receiving end of the needle hub is configured to connect to and receive an injection device and the slidable sleeve is adapted to slide in the direction of the length of the needle between an extended position in which the needle tip is located inside the slidable sleeve and a retracted position in which the needle tip projects from the slidable sleeve, via an intermediate position between the extended position and the retracted position in which the slidable sleeve is releasably held in the intermediate position by engagement of the catch and projection, such that, in use, the slidable sleeve is moved into the intermediate position for injection into the patient by sliding along a tapering interior surface of the needle hub and then as the needle is inserted into the patient, the slidable sleeve is released from the intermediate position and caused to move into the retracted position, and in moving into the retracted position, a resultant force is generated, such that, on removal of the needle from the patient, the resultant force causes the slidable sleeve to move towards the injection end of the needle hub and into the extended position, the safety needle further comprising a locking mechanism capable of retaining the slidable sleeve in the extended position after removal of the needle from the patient, and
   wherein the pack covers at least the needle tip in the intermediate position, and by causing the pack to be moved in a direction towards the receiving end of the needle hub from the storage position to the intermediate position, the pack engages the slidable sleeve which is retracted from the extended position to the intermediate position, the pack being removable from the needle hub and slidable sleeve in the intermediate position.

2. The safety needle as claimed in claim 1, wherein the receiving end of the pack includes an open portion covered by a releasable membrane.

3. The safety needle as claimed in claim 2, wherein the releasable membrane is gas permeable.

4. The safety needle as claimed in claim 1, wherein the injection end of the pack has an extended portion which is capable of housing the needle tip in the intermediate position.

5. The safety needle as claimed in claim 1, wherein the needle hub has one or more projections which abut against one or more shoulders on the inside of the pack when the slidable sleeve is in the intermediate position.

6. The safety needle as claimed in claim 1, wherein the needle hub has an outer surface which is adapted to deflect the slidable sleeve as, in use, the needle is inserted into the patient, and the slidable sleeve has a radially elastically deformable portion such that, in use, the resultant force is generated within the slidable sleeve as the slidable sleeve is caused to move towards the receiving end of the needle hub and into the retracted position.

7. The safety needle as claimed in claim 6, wherein the slidable sleeve has at least one cantilever arm which engages a helical track in the outer surface of the needle hub such that, in use, as the needle is inserted into a patient, the at least one cantilever arm is displaced radially by the helical track in the outer surface of the needle hub thereby generating the resultant force.

8. The safety needle as claimed in claim 6, wherein the safety needle has two to six cantilever arms.

9. The safety needle as claimed in claim 6, wherein the receiving end of the slidable sleeve has elastic properties and, in use, as the needle is inserted into a patient, the resultant force is generated within the slidable sleeve.

10. The safety needle as claimed in claim 1, wherein at least part of the receiving end of the needle hub has a tapered outer surface which tapers towards the injection end and the slidable sleeve has a radially elastically expandable portion.

11. The safety needle as claimed in claim 10, wherein the outer surface of the receiving end of the needle hub has a substantially conical shape which tapers towards the injection end.

12. The safety needle as claimed in claim 10, wherein the slidable sleeve has at least one cantilever arm which bears resiliently on the tapered outer surface of the needle hub and, in use, as the needle is inserted into a patient, the at least one cantilever arm is displaced outwards by the tapered outer surface of the needle hub thereby generating the resultant force.

13. The safety needle as claimed in claim 1, wherein the locking mechanism provides substantially no resistance against the resultant force as the slidable sleeve moves from the retracted position to the extended position.

14. The safety needle as claimed in claim 1, wherein the slidable sleeve has a first extended position where the slidable sleeve is able to be moved towards the receiving end of the needle hub and a second extended position where the slidable sleeve is in a locked position.

15. The safety needle as claimed in claim 14, wherein the locking mechanism comprises a latching pawl on the inside surface of the slidable sleeve capable of latching to a shoulder on the outside surface of the needle hub when the slidable sleeve is in the second extended position.

16. The safety needle as claimed in claim 14, wherein an inside surface of the slidable sleeve has a pin which engages a sprag and a resilient pawl attached to the needle hub thereby holding the slidable sleeve in the first extended position and, in use, allowing the slidable sleeve to move into the second extended position.

17. The safety needle as claimed in claim 1, wherein the locking mechanism comprises one or more projections on the slidable sleeve and a corresponding one or more holes on the needle hub such that in the extended position, after removal from the patient, the one or more projections lockably engage the corresponding one or more holes.

18. The safety needle as claimed in claim 17, wherein the one or more holes on the needle hub is a circumferentially continuous hole.

19. The safety needle as claimed in claim 1, wherein the slidable sleeve, prior to use, is not under any substantial load.

20. The safety needle as claimed in claim 1, wherein the needle tip is at least partially shrouded in the intermediate position.

21. The safety needle as claimed in claim 1, wherein the needle tip projects from the slidable sleeve in the intermediate position.

22. The safety needle as claimed in claim 1, wherein the needle hub further includes an indent having the tapering interior surface, wherein the indent is spaced apart from the catch and when in the storage position the needle tip is located inside the slidable sleeve and the projection is engaged with the indent.

23. A safety needle for use with an injection device comprising:
- a needle having a needle tip for injecting into a patient;
- a needle hub having
  - an injection end mounted to and partially surrounding the needle,
  - a receiving end configured to mount to and receive the injection device, and
  - a catch on a surface of the needle hub;
- a slidable sleeve having
  - a projection extending from the slidable sleeve,
  - an injection end slidable over the needle, and
  - a proximal end slidably mounted on and slidable along the needle hub, the slidable sleeve slidable along the needle hub between an initial position and a retracted position by sliding along a tapering interior surface of the needle hub, the needle tip projecting from the slidable sleeve in the retracted position, the slidable sleeve having an intermediate position between an extended position and the retracted position in which the slidable sleeve is releasably held in the intermediate position by engagement of the catch and projection, wherein injecting the needle into the patient releases the slidable sleeve from the intermediate position and toward the retracted position, the slidable sleeve being spring biased with respect to the needle hub in the retracted position such that, upon removal of the needle from the patient, the proximal end of the slidable sleeve moves toward the injection end of the needle hub and into the extended position in which the slidable sleeve covers the needle tip and the proximal end of the slidable sleeve is no longer slidable along the needle hub; and
- a pack surrounding the needle, the needle hub and the slidable sleeve in the initial position, the needle hub and needle movable within the pack such that urging the pack toward the receiving end of the needle hub urges the slidable sleeve from the initial position into the intermediate position, the pack covering the needle tip in the intermediate position and being removably secured to the needle, the needle hub and the slidable sleeve by friction while the slidable sleeve remains in the intermediate position.

24. The safety needle as claimed in claim 23, wherein the pack completely surrounds the needle, the needle hub and slidable sleeve in the initial position.

25. The safety needle as claimed in claim 23, wherein the needle hub has an outer surface which is tapered from the receiving end toward the injection end and radially deflects the slidable sleeve as the slidable sleeve moves from the intermediate position to the retracted position generating the spring bias between the slidable sleeve and the needle hub.

26. The safety needle as claimed in claim 23, wherein the needle hub further includes an indent having the tapering interior surface, wherein the indent is spaced apart from the catch and wherein the slidable sleeve is movable between the initial position and the retracted position by sliding along the tapering interior surface of the indent.

* * * * *